United States Patent [19]

Delmas et al.

[11] Patent Number: 4,591,651

[45] Date of Patent: May 27, 1986

[54] PROCESS FOR DIRECTLY CONVERTING AN ALDEHYDE INTO AN ETHYLENE ESTER

[75] Inventors: Michel Delmas, Montgiscard; Antoine Gaset, Toulouse; Yves Le Bigot, Bragassargues, all of France

[73] Assignee: Agrifurane S.A., France

[21] Appl. No.: 654,497

[22] Filed: Sep. 26, 1984

[30] Foreign Application Priority Data

Sep. 30, 1983 [FR] France .............................. 83 15753

[51] Int. Cl.$^4$ ..................... C07C 67/00; C07D 307/54
[52] U.S. Cl. .................................. 549/473; 549/499; 560/75; 560/104; 560/210
[58] Field of Search .................. 549/473, 499; 560/75, 560/104, 210

[56] References Cited

U.S. PATENT DOCUMENTS

| 4,346,040 | 8/1982 | Delmas et al. ...................... 549/506 |
| 4,501,910 | 2/1985 | Delmas et al. ...................... 549/499 |

*Primary Examiner*—Richard L. Raymond
*Attorney, Agent, or Firm*—Harold H. Dutton, Jr.

[57] ABSTRACT

The invention concerns a process for directly converting an aldehyde into an ethylene ester, of the type wherein the aldehyde is placed in the presence of an alkaline carbonate or bicarbonate and of a phosphonate into a solvent with an alcohol function. In the invention, an ethyl phosphonate or a methyl phosphonate is used and the solvent is an alcohol or a polyol including a hydrocarbon radical other than ethyl or methyl, this radical being that of the ethylenic ester to be produced. The process of the invention makes it possible to directly convert furan aldehyde or tetrahydrofuran aldehyde to produce an ethylenic ester with a furan ring or a tetrahydrofuran ring.

7 Claims, No Drawings

PROCESS FOR DIRECTLY CONVERTING AN ALDEHYDE INTO AN ETHYLENE ESTER

The invention concerns a process for directly converting an aldehyde into an ethylene ester; in particular it applies to converting furan aldehydes or tetrahydrofuran aldehydes.

BACKGROUND AND OBJECTS

It is known that presently the WITTIG-HORNER reaction is used to produce alkenes from aldehydes and to introduce acid, ester, nitrile, etc . . . functions on the ethylenic double bond. The object of this reaction is the preparation of an ethylene ester and comprises placing the initial aldehyde in the presence of the following reagents: phosphonate and base, in an inert organic solvent (J. SEYDEN-PENNE et al, Tetrahedron, 1972, p 4209; Tetrahedron, 1973, p 2437, and Journal of Organic Chemistry, 1980, p 1270; C. PIECHUCKI, Synthesis, 1974, 869; M. MIKOLAJCZYK et al, Synthesis, 1976, p396; J. KOVAC et al, Collection Czechoslovakia Chemical Communications, 1976, p 764; E. BREUER et al, Tetrahedron, 1978, p 924; A. FOUCAUD et al, Tetrahedron Letters, 1980, p 2161 and Synthesis, 1979, p 884; J. VILLERAS et al, Synthesis, 1983, p 300 and Phosphorus and Sulfur, 1983, p 385). An improved method is described in the French patent application #81.17825 and U.S. Pat. No. 4,501,910 in the name of applicant; this method employs an alcohol as the solvent.

In all these methods, the base allows taking a porton off the phosphorus' alpha-carbon. The reactive entity so formed condenses with the aldehyde carbonyl function to result in an intermediary oxy-anion which thereafter changes toward the ethylene ester. Rigorously speaking the organic solvent does not constitute a reagent of this reaction and is not used up in it even if the method of the application No. 81.17825 and U.S. Pat. No. 4,501,910 is improved by this solvent as to the yield of the desired type of alkene.

The above cited reactions necessarily result in an ethylenic ester of which the radicals are obtained from the phosphonate. However, presently few phosphonates are commercially available and as a matter of fact, with respect to low-cost products, solely the methyl or ethyl phosphonates are commercially offered. Accordingly only the ethylene esters of methyl or ethyl given by the formula below

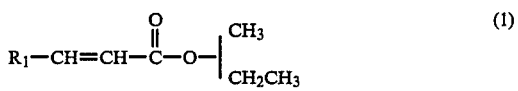

$$R_1-CH=CH-\overset{O}{\underset{\|}{C}}-O-\begin{vmatrix} CH_3 \\ CH_2CH_3 \end{vmatrix} \qquad (1)$$

have been synthesized by the WITTIG-HORNER and derivative reactions.

Of course it is always possible to substitute thereafter the ethyl or methyl radical by a new and desired radical by means of a transesterification reaction. However this double reaction requires a first extraction of the ethyl or methyl ethylene ester at the end of the WITTIG-HORNER reaction and then a second extraction with the object of isolating the desired ethylene ester. Besides the constraints resulting from implementing two consecutive reactions, this procedure also results in a notable drop in yields because the overall yield is the product of the particular yields of the two reactions and the two extractions.

An object of the present invention is to eliminate the above-stated limmitations placed on the WITTIG-HORNER reaction by creating a process allowing to convert directly, and in a single operation which is free of any intermediate separation, an aldehyde into an ethylene ester of the formula

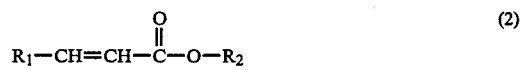

$$R_1-CH=CH-\overset{O}{\underset{\|}{C}}-O-R_2 \qquad (2)$$

where $R_2$ is a hydrocarbon radical other than methyl or ethyl and selected by the operator.

Another object of the invention is to create a conversion procedure which allows a very high yield of ethylenic ester.

DESCRIPTION OF THE INVENTION

Accordingly the process object of the invention is of the type wherein an aldehyde is placed into the presence of a phosphonate and an alkaline carbonate or bicarbonate in a solvent comprising an alcohol function; according to the present invention, in order to produce an ethylene ester of the formula:

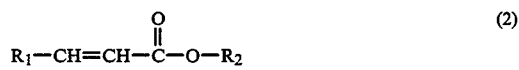

$$R_1-CH=CH-\overset{O}{\underset{\|}{C}}-O-R_2 \qquad (2)$$

where $R_1$ is a hydrogen or a radical or a hydrocarbon ring from the initial aldehyde, and more particularly is hydrogen, furyl, tetrahydrofuryl, nitro-5-furyl, phenyl, p-hydroxyphenyl, or butyl, and where $R_2$ is a hydrocarbon radical other than methyl or ethyl, the following are used:

on one hand an ethyl or methyl phosphonate of the formula:

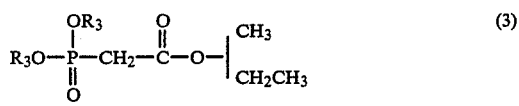

$$R_3O-\overset{OR_3}{\underset{\underset{O}{\|}}{P}}-CH_2-\overset{O}{\underset{\|}{C}}-O-\begin{vmatrix} CH_3 \\ CH_2CH_3 \end{vmatrix} \qquad (3)$$

where $R_3$ is a hydrocarbon ring or radical, more particularly methyl or ethyl on the other hand an alcohol or an $R_2OH$ polyol including the hydrocarbon radical $R_2$, other than methyl or ethyl, of the ethylene ester to be prepared.

The inventors have shown that surprisingly on one hand the alcohol or the polyol, which hitherto was restricted to be merely solvents, now may be both solvent and reagent by selecting them with a radical different from that of the phosphonate, and on the other hand under the above stated conditions, the alkaline bicarbonate or carbonate furthermore may assume, other than its conventional role of reagent in the WITTIG-HORNER reaction, also the function of a catalyst when exchanging the ethyl and methyl radicals by the desired $R_2$ radical.

The process of the invention makes use of both phenomena (without as yet a possible determination whether these are simultaneous or consecutive) and allows producing highly diverse ethylenic esters with excellent yields and selectivities as shown by experiment. This remarkable result is due to the unusual combination of the following features:

reagent/catalyst for the carbonate and bicarbonate, reagent/solvent for the alcohol and polyol.

To enhance these two features, the process is advantageously implemented under the following conditions:

the alkaline carbonate or bicarbonate is used in such an amount that its molar ratio with respect to the aldehyde exceeds unity, and the alcohol or polyol is used in such an amount that their molar ratio with respect to the aldehyde exceeds 2.

Thus the amounts of the above stated two substances are adjusted so they can fully perform their dual roles (that is, providing a good yield for each implemented phenomenon).

Further, in order to still increase the yield, while nevertheless retaining easily implemented conditions, the hydration rate of the reaction medium is limited to between approximately 0.1 and 5 moles of water per mole of aldehyde.

The most common ethyl and methyl phosphonates and the most economical ones are those wherein the radical $R_3$ also is an ethyl or methyl radical. For economic reasons, this type of radical $R_3$ will be preferred.

The above stated direct conversion reaction can be carried out at atmospheric pressure.

It is also possible to operate at reduced pressure, whereby the yield is substantially improved. In practice a pressure between 10 and 200 mm Hg (1,315 and 26 300 Pascals) may be provided.

The alcohol used can be a polyol wherein the $R_2$ radical contains between 1 and 5 alcohol functions in order to obtain hydroxylated ethylenic esters. In addition, a fatty alcohol with a long chain radical $R_2$ with a number of carbons equal to or greater than 8 can be used to prepare an ethylester comprising a lipophilic chain. In other words, the alcohol or polyol may be described as $R_2(OH)_n$, in which $R_2$ is propyl, butyl, furfuryl, tetrahydrofurfuryl, benzyl, or long chain fatty alkyl having at least 8 carbon atoms, and in which n is 1 to 5.

DESCRIPTION OF PREFERRED EMBODIMENTS

The examples below illustrate the process of the invention when implemented at atmospheric pressure (Examples 1 through 14) and when implemented at reduced pressure (Examples 15–18).

As will be shown by these examples, the process of the invention makes it possible to synthesize molecules of the following formulas:

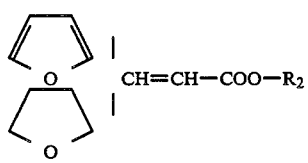

where $R_2$ is a hydrocarbon ring or radical;

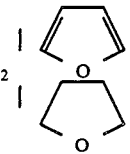

where $R_1$ is a hydrocarbon ring or a radical or hydrogen; and

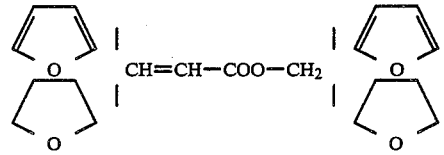

$R_1-CH=CH-COO-R_2$ where $R_1$ is hydrogen or a hydrocarbon ring or radical, and $R_2$ is a long chain hydrocarbon radical with a number of carbons equal to or exceeding 8, or a radical or hydrocarbon ring comprising between 1 and 5 alcohol functions.

EXAMPLE 1

Direct synthesis of furfurylidene-2-propylacetate from furfural and diethyl phosphonoethylacetate in the presence of potassium carbonate in propanol.

0.02 moles of furfural, 0.08 moles of potassium carbonate, 0.025 moles of diethylphosphono-ethylacetate are placed in a 100 ml reactor in 0.5 moles of propanol.

The reaction medium is agitated for 3 h at a temperature of 25° C.

At the end of the reaction, the solid phase is separated by simple filtration. The organic phase is reduced using the rotovapor. The crude reaction product so obtained is purified on a MERCK silica gel column by means of a ether/hexane mixture acting as the eluent.

The result is a molecule which can be denoted by the chemical name "furfurylidene-2-propylacetate" of the formula

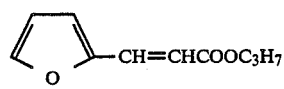

This substance is prepared with a yield of 83% and was identified by its magnetic resonance spectroscopy of the proton and carbon 13 and its infrared and ultraviolet spectra. As for all the examples below, it was noted that the E-type ethylenic ester is preferentially obtained (in a proportion exceeding 90%).

EXAMPLE 2

Direct synthesis of furfurylidene-2-furfurylacetate from furfural and diethylphosphonoethylacetate in the presence of potassium carbonate in furfurylic alcohol.

0.03 moles of furfural, 0.07 moles of potassium carbonate, 0.035 moles of diethylphosphono-ethylacetate are placed into a 100 ml reactor in 0.25 moles of furfurylic alcohol.

The reaction medium is agitated for 4 h at a temperature of 60° C.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as being "furfurylidene-2-furfurylacetate" of which the formula is:

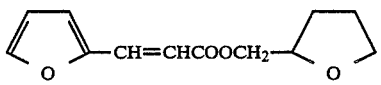
(8)

This substance is obtained in pure form with a yield of 81% and was identified by its magnetic resonance spectroscopy of the proton and carbon 13 and its infrared and ultraviolet spectroscopy.

EXAMPLE 3

Direct synthesis of furfurylidene-2-tetrahydrofurfuryl acetate from tetrahydrofurfural and dimethylphosphono-methylacetate in the presence of cesium carbonate in tetrahydrofurfuryl alcohol.

0.02 moles of tetrahydrofurfural, 0.06 moles of cesium carbonate, 0.025 moles of dimethylphosphono-methylacetate are placed into a 100 ml reactor in 0.25 moles of tetrahydrofurfuryl alcohol.

The reaction medium is agitated for 5 h at a temperature of 50° C.

At the end of the reaction, the solid phase is separated by simple filtration. The organic phase is reduced using the rotavapor. The crude reaction product so obtained is purified in a MERCK silica gel column using a mixture of etherhexane as the eluent.

A molecule is obtained which can be denoted chemically as "furfurylidene-2-tetrahydrofurfurylacetate" of the formula

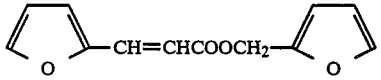
(9)

This substance is produced in pure form with a yield of 84% and was identified by its magnetic resonance spectroscopy the proton and carbon 13 and its infrared and ultraviolet spectroscopy.

EXAMPLE 4

Direct synthesis of furfurylidene-2-furfurylacetate from furfural and diethylphosphonoethylacetate in the presence of rubidium carbonate in furfuryl alcohol.

0.02 moles of furfural, 0.05 moles of rubidium carbonate, 0.03 moles of diethylphosphono-ethylacetate are placed into a 100 ml reactor in 0.2 moles of furfuryl alcohol.

The reaction medium is agitated for 3 h at a temperature of 65° C.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as being "furfurylidene-2-furfurylacetate" and the formula of which is shown in Example 2.

This substance is obtained in pure form with a yield of 87% and was identified by its magnetic resonance spectroscopy of the proton and carbon 13 and its infrared and ultraviolet spectra.

EXAMPLE 5

Direct synthesis of furfurylidene-2-butylacetate from furfural and dimethylphosphonomethylacetate in the presence of potassium carbonate in butanol.

0.3 moles of furfural, 0.08 moles of potassium carbonate, 0.035 moles of dimethylphosphono-methylacetate are placed into a 100 ml reactor in 0.4 moles of butanol.

The reaction medium is agitated for 3 h at a temperature of 70° C.

At the end of the reaction the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as being "furfurylidene-2-butylacetate" and of which the formula is

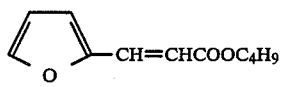
(10)

This substance is obtained in pure form with a yield of 80% and was identified by the its magnetic resonance spectroscopy of the proton and carbon 13, and by infrared and ultraviolet spectroscopy.

EXAMPLE 6

Direct synthesis of furfurylidene-2-octylacetate from furfural and diethylphosphono-ethylacetate in the presence of potassium carbonate in 1-octanol.

0.02 moles of furfural, 0.05 moles of potassium carbonate, 0.025 moles of diethylphosphono-ethylacetate are placed into a 100 ml reactor in 0.25 ml of 1-octanol.

The reaction medium is agitated for 5 h at a temperature of 60° C.

At the end of the reaction, the solid phase is separated by simple filtration. The organic phase is reduced using the rotavapor. The crude reaction product so obtained is purified in MERCK silica gel column using a mixture of ether and hexane as the eluent.

A molecule is obtained which can be chemically denoted as being "furfurylidene-2-octylacetate" and of the formula:

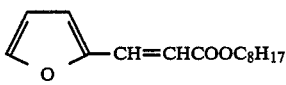
(11)

This substance is obtained in pure form with a yield of 78% and was identified by its magnetic resonance spectroscopy of the proton and carbon 13, and by its infrared and ultraviolet spectroscopy.

EXAMPLE 7

Direct synthesis of furfurylidene-2-hexadecylacetate from furfural and diethylphosphonoethylacetate in the presence of potassium carbonate in 1-hexadecanol.

0.02 moles of furfural, 0.06 moles of potassium carbonate, 0.025 moles of diethylphosphono-ethylacetate are placed into a 100 ml reactor in 0.25 moles of 1-hexadecanol.

The reaction medium is agitated for 6 h at a temperature of 70° C.

At the end of the reaction, the solid phase is separated by simple filtration. The organic phase is reduced using the rotavapor. The crude reaction product so obtained is purified in MERCK silica gel column using a mixture of ether and hexane as the eluent.

A molecule is obtained which can be chemically denoted as being "furfurylidene-2-hexadecylacetate" and of which the formula is $$\text{furan}-CH=CHCOOC_{16}H_{31} \quad (12)$$

This substance is obtained in pure form with a yield of 80% and was identified by the magnetic resonance spectroscopy of the proton and carbon 13, and by its infrared and ultraviolet spectroscopy.

EXAMPLE 8

Direct synthesis of 5-nitrofurfurylidene-2-furfurylacetate from 5-nitrofurfural and diethylphosphono-ethylacetate in the presence of potassium carbonate in furfuryl alcohol.

0.03 moles of nitro-5 furfural, 0.04 moles of potassium carbonate, 0.035 moles of diethylphosphono-ethylacetate are placed into a 100 ml reactor in 0.3 moles of furfuryl alcohol.

The reaction medium is agitated for 2 h at 50° C.

At the end of the reaction, the solid phase is separated by simple filtration. The organic phase is reduced using the rotavapor. The crude reaction product so obtained is purified using a MERCK silica gel column with a mixture of ether and hexane as the eluent.

A molecule is obtained which can be chemically denoted as being "5-nitro-furfurylidene-2-furfurylacetate" and of which the formula is given by $$O_2N-\text{furan}-CH=CHCOOCH_2-\text{furan} \quad (13)$$

This substance is obtained in pure form with a yield of 79% and was identified by its magnetic resonance spectroscopy of the proton and carbon 13, and its infrared and ultraviolet spectroscopy.

EXAMPLE 9

Direct synthesis of butyl cinnamate from benzaldehyde and diethylphosphono-ethylacetate in the presence of potassium carbonate in a mixture of water and butanol.

0.02 moles of benzaldehyde, 0.06 moles of potassium carbonate, 0.03 moles of diethylphosphono-ethylacetate are placed into a 100 ml reactor in a mixture of 0.1 moles of water and 0.3 moles of butanol.

The reaction medium is agitated for 2 h at a temperature of 60° C.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as being "butyl cinnamate" and of which the formula is:

$$\text{phenyl}-CH=CHCOOC_4H_9 \quad (14)$$

The substance so produced is obtained in pure form with a yield of 86% and was identified by its magnetic resonance spectroscopy of the proton and carbon 13 and its infrared and ultraviolet spectroscopy.

EXAMPLE 10

Direct synthesis of furfuryl cinnamate from benzaldehyde and diethylphosphono-ethylacetate in the presence of potassium carbonate in furfuryl alcohol.

0.03 moles of benzaldehyde, 0.08 moles of potassium carbonate, 0.04 moles of diethylphosphono-ethylacetate are placed into a 100 ml reactor in a mixture of 0.1 moles of dioxane and 0.2 moles of furfuryl alcohol.

The reaction medium is agitated for 4 h at a temperature of 70° C.

At the end of the reaction, the solid phase is separated by simple filtration. The organic phase is reduced using the rotavapor. The crude reaction product so obtained is purified in a MERCK silica gel column using a mixture of ether and hexane as the eluent.

A new molecule is obtained which can be chemically designated as being "furfuryl cinnamate" and of which the formula is given by $$\text{phenyl}-CH=CHCOOCH_2-\text{furan} \quad (15)$$

This substance is obtained in pure form with a yield of 80% and was identified by its magnetic resonance spectroscopy of the proton and carbon 13, and by its infrared and ultraviolet spectroscopy.

EXAMPLE 11

Direct synthesis of p-hydroxybutylcinnamate from p-hydroxybenzaldehyde and diethylphosphonoethylacetate in the presence of potassium carbonate in butanol.

0.02 moles of p-hydroxybenzaldehyde, 0.06 moles of potassium carbonate, 0.025 moles of diethylphosphono-ethylacetate are placed into a 100 ml reactor in 0.3 moles of butanol.

The reaction medium is agitated for 3 h at a temperature of 50° C.

At the end of the reaction the solid phase is separated by simple filtration. The organic phase is reduced using the rotavapor. The crude reaction product so obtained is purified in a MERCK silica gel column using a mixture of ether/hexane as the eluent.

A molecule is obtained which can be chemically denoted as being "p-hydroxybutylcinnamate" of the formula:

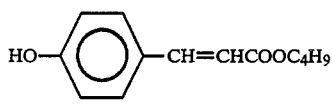

(16)

This substance is obtained in pure form with a yield of 77% and was identified by its magnetic resonance spectroscopy of the proton and carbon 13 and by its infrared and ultraviolet spectroscopy.

EXAMPLE 12

Direct synthesis of furfuryl butanoate from butanal and diethylphosphono-ethylacetate in the presence of potassium carbonate in furfuryl alcohol.

0.02 moles of butanal, 0.06 moles of potassium carbonate, 0.025 moles of diethylphosphono-ethylacetate are placed into a 100 ml reactor in 0.25 moles of furfuryl alcohol, and the reaction medium is agitated for 2 h at a temperature of 40° C.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as being "furfuryl butanoate" and of which the formula is

(17)

This substance is obtained in pure form with a yield of 82% and was identified by its magnetic resonance spectroscopy of the proton and carbon 13, and by its infrared and ultraviolet spectroscopy.

EXAMPLE 13

Direct synthesis of furfuryl acrylate from 35% aqueous formaldehyde and diethylphosphono-ethylacetate in the presence of potassium carbonate in furfuryl alcohol.

0.02 moles of formaldehyde in 35% aqueous solution, 0.06 moles of potassium carbonate, 0.025 moles of diethylphosphono-ethylacetate are placed into a 100 ml reactor in 0.35 moles of furfuryl alcohol, and the reaction medium is agitated for 3 h at a temperature of 60° C.

At the end of the reaction, the solid phase is separated by simple filtration. The organic phase is reduced using a rotavapor. The crude reaction product so obtained is purified in a MERCK silica gel column using a mixture of ether/hexane as the eluent. A molecule is obtained which can be chemically denoted as "furfuryl acrylate" and of which the formula is as follows:

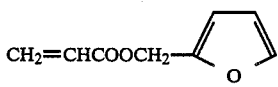

(18)

This substance is obtained in pure form with a yield of 85% and was identified by its magnetic resonance spectrosopy of the proton and carbon 13, and by its infrared and ultraviolet spectroscopy.

EXAMPLE 14

Direct synthesis of butyl acrylate from paraformaldehyde and diethylphosphono-ethylacetate in the presence of potassium carbonate in butanol.

0.03 moles of formaldehyde in the form of paraformaldehyde, 0.08 moles of potassium carbonate, 0.035 moles of diethylphosphono-ethylacetate are placed into a 100 ml reactor in 0.3 moles of butanol and the reaction medium is agitated for 3 h at a temperature of 60° C.

At the end of the reaction, the solid phase is separated by simple filtration. The organic phase is reduced using a rotavapor. The crude reaction product so obtained is purified in a MERCK silica gel column using a mixture of ether and hexane as the eluent.

A molecule is obtained which can be chemically denoted as "butyl acrylate" and of which the formula is:

$$CH_2=CHCOOC_4H_9 \qquad (19)$$

This substance is obtained in pure form with a yield of 80% and was identified by its magnetic resonance spectroscopy of the proton and carbon 13, and by its infrared and ultraviolet spectroscopy.

EXAMPLE 15

Direct synthesis of furfurylidene-2-(1-methyl, 2-hydroxy)propylacetate from furfural and dimethylphosphono-methylacetate in the presence of potassium carbonate in 2,3-butanediol.

0.5 moles of furfural, 1 mole of potassium carbonate, 0.6 moles of dimethylphosphono-methylacetate are placed into a 250 ml reactor in 3 moles of 2,3-butanediol.

The reaction medium is agitated under a partial vacuum of 200 mm Hg (26,300 Pascals) for 2 h at a temperature of 60° C. The methyl alcohol formed is distilled off continuously during the reaction and is recovered by means of a DEAN-STARK apparatus.

At the end of the reaction, the solid phase is separated by simple filtration. The organic phase is reduced using a rotavapor. The crude reaction product so obtained is purified in a MERCK silica gel column using a mixture of ether and hexane as the eluent.

A molecule is obtained which may be chemically denoted as "furfurylidene-2-(1-methyl, 2-hydroxy)propylacetate" and of which the formula is

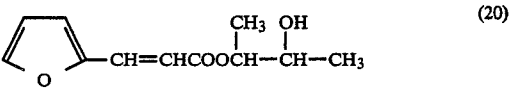

(20)

This substance is obtained in pure form with a yield of 70% and was identified by its magnetic resonance spectroscopy of the proton and carbon 13 and its infrared and ultraviolet spectroscopy.

EXAMPLE 16

Direct synthesis of furfurylidene-2-benzylacetate from furfural and diethylphosphono-ethylacetate in the presence of potassium carbonate in benzyl alcohol.

0.5 moles of furfural, 0.7 moles of potassium carbonate, 0.6 moles of diethylphosphono-ethylacetate are placed into a 250 ml reactor in 2 moles of benzyl alcohol.

The reaction medium is agitated under a partial vacuum of 50 mm Hg (6,575 Pascals) for 3 h at 50° C. The ethyl alcohol formed continuously distills off during the reaction and is recovered using a DEAN-STARK apparatus.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as "furfurylidene-2-benzylacetate" and of the formula:

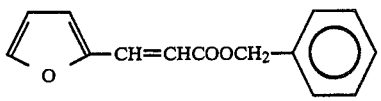
(21)

This substance is obtained in pure form with a yield of 92% and was identified by its magnetic resonance spectroscopy of the proton and carbon 13 and by its infrared and ultraviolet spectroscopy.

EXAMPLE 17

Direct synthesis of tetrahydrofurfurylidene-2-furfurylacetate from tetrahydrofurfural and diethylphosphono-ethylacetate in the presence of potassium carbonate in furfuryl alcohol.

0.5 moles of tetrahydrofurfural, 0.9 moles of potassium carbonate, 0.6 moles of diethylphosphono-ethylacetate are placed into a 250 ml reactor in 2 moles of furfuryl alcohol.

The reaction medium is agitated under a partial vacuum of 200 mm Hg (26,300 Pascals) for 3 h at 60° C. The formed ethyl alcohol distills off continuously during the reaction and is recovered by means of a DEAN-STARK apparatus.

At the end of the reaction, the solid phase is separated by simple filtration. The organic phase is reduced using a rotavapor. The crude reaction product so obtained is purified in a MERCK silica gel column using a mixture of ether and hexane as the eluent.

A molecule is obtained which can be chemically denoted as being "tetrahydrofurfurylidene-2-furfurylacetate" and of which the formula is:

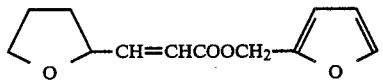
(22)

This substance is obtained in pure form with a yield of 88% and was identified by the magnetic resonance spectroscopy of the proton and carbon 13, and by its infrared and ultraviolet spectroscopy.

EXAMPLE 18

Direct synthesis of furfurylidene-2 furfurylacetate from furfural and diethylphosphono-ethylacetate in the presence of potassium carbonate in furfuryl alcohol.

0.5 moles of furfural, 0.9 moles of potassium carbonate, 0.6 moles of diethylphosphono-ethylacetate are placed into a 250 ml reactor in 2 moles of furfuryl alcohol.

The reaction medium is agitated under a partial vacuum of 200 mm Hg (26,300 Pascals) for 3 h at 60° C. The ethyl alcohol formed distills off continuously during the reaction and is recovered by means of a DEAN-STARK apparatus.

At the end of the reaction, the solid phase is separated by simple filtration. The organic phase is reduced using the rotavapor. The crude reaction product so obtained is purified in a MERCK silica gel column using a mixture of ether and hexane as the eluent.

A molecule is obtained which can be chemically denoted as "furfurylidene-2-furfurylacetate" and of which the formula is already provided in Example 2.

This substance is obtained in pure form with a yield of 92% and was identified by its magnetic resonance spectroscopy of the proton and carbon 13, and by its infrared and ultraviolet spectroscopy.

We claim:

1. A process for directly converting an aldehyde of the formula $R_1CHO$ into an ethylenic ester of the formula:

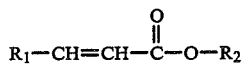

the process comprising reacting said aldehyde in the presence of a phosphonate of the formula

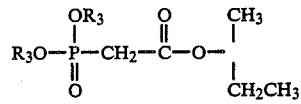

and in the presence of an alkaline carbonate or alkaline bicarbonate with an alcohol or polyol solvent of the formula $R_2(OH)_n$, wherein $R_1$ is hydrogen, furyl, tetrahydrofurfuryl, nitro-5-furyl, phenyl, p-hydroxyphenyl or butyl, $R_2$ is propyl, butyl, furfuryl, tetrahydrofurfuryl, benzyl, or long chain fatty alkyl having at least 8 carbon atoms, and n is 1 to 5, and $R_3$ is methyl or ethyl, and wherein the molar ratio of said alkaline carbonate or alkaline bicarbonate to said aldehyde is greater than one, and the molar ratio of said alcohol or polyol solvent to said aldehyde is greater than two.

2. A direct conversion process as in claim 1 wherein the hydration rate of the reaction medium is approximately between 0.1 and 5 moles of water per mole of aldehyde.

3. A process as in claim 1 characterized in that the direct conversion reaction is carried out at a pressure between 10 and 200 mm Hg (1,315 and 26,300 Pascals).

4. A process as in claim 1 for the direct transformation of furan aldehyde or tetrahydrofuran aldehyde for producing an ethylenic ester of which the $R_1$ radical includes a furan ring

or a tetrahydrofuran ring

5. A direct conversion process as in claim 4 wherein said alcohol is selected from the group consisting of furfuryl alcohol and tetrahydrofurfuryl alcohol.

6. A process as in claim 1 characterized in that a polyol is used wherein the $R_2$ radical contains between 1 and 5 alcohol functions.

7. A process as in claim 1 and wherein said solvent comprises a long chain fatty alcohol having at least 8 carbon atoms per molecule.

* * * * *